(12) United States Patent
Tessarolo et al.

(10) Patent No.: US 12,357,234 B2
(45) Date of Patent: Jul. 15, 2025

(54) SENSORIZED GARMENT

(71) Applicants: LET'S—WEBEARABLE SOLUTIONS S.R.L. IN BREVE LET'S - S.R.L., L'Aquila (IT); UNIVERSITÀ DEGLI STUDI DI CAGLIARI, Cagliari (IT); ALMA MATER STUDIORUM—UNIVERSITÀ DI BOLOGNA, Bologna (IT)

(72) Inventors: Marta Tessarolo, Bologna (IT); Giuseppe Arnaldo Usai, L'Aquila (IT); Danilo Pani, Cagliari (IT); Annalisa Bonfiglio, Cagliari (IT); Eleonora Sulas, Cagliari (IT); Beatrice Fraboni, Bologna (IT)

(73) Assignees: LET'S—WEBEARABLE SOLUTIONS S.R.L. IN BREVE LET'S—S.R.L., L'Aquila (IT); UNIVERSITÀ DEGLI STUDI DI CAGLIARI, Cagliari (IT); ALMA MATER STUDIORUM—UNIVERSITÀ DI BOLOGNA, Bologna (IT)

( * ) Notice: Subject to any disclaimer, the term of this patent is extended or adjusted under 35 U.S.C. 154(b) by 779 days.

(21) Appl. No.: 17/311,400

(22) PCT Filed: Dec. 5, 2019

(86) PCT No.: PCT/IB2019/060496
§ 371 (c)(1),
(2) Date: Jun. 7, 2021

(87) PCT Pub. No.: WO2020/115708
PCT Pub. Date: Jun. 11, 2020

(65) Prior Publication Data
US 2022/0022815 A1 Jan. 27, 2022

(30) Foreign Application Priority Data

Dec. 7, 2018 (IT) .................... 102018000010886

(51) Int. Cl.
*A61B 5/00* (2006.01)
*A41D 1/00* (2018.01)
*A61B 5/0205* (2006.01)

(52) U.S. Cl.
CPC .......... *A61B 5/6805* (2013.01); *A41D 1/002* (2013.01); *A61B 5/0205* (2013.01);
(Continued)

(58) Field of Classification Search
None
See application file for complete search history.

(56) References Cited

U.S. PATENT DOCUMENTS

2012/0323501 A1* 12/2012 Sarrafzadeh .............. G01L 1/18
702/41
2018/0255845 A1* 9/2018 Eisenhuth ............... A41F 19/00
2018/0279930 A1* 10/2018 Coppedè ................ C12Q 1/002

FOREIGN PATENT DOCUMENTS

WO WO-9505119 A2 * 2/1995 ........... A61B 5/1135
WO WO-2005027720 A2 * 3/2005 ........... A61B 5/0205
(Continued)

OTHER PUBLICATIONS

Lu et al., QRS Detection Based on Improved Adaptive Threshold, pp. 1-8, printed on Jul. 10, 2024 (Year: 2018).*

*Primary Examiner* — Daniel L Cerioni
*Assistant Examiner* — Om Patel
(74) *Attorney, Agent, or Firm* — Bayramoglu Law Offices LLC

(57) ABSTRACT

A sensorized garment is provided. The sensorized garment includes an wearable element on a skin having a hand-tightening or a closure device to securely constrain sensors,
(Continued)

for example electrodes to detect electrophysiological signals, during a physical activity. The wearable element has a three-dimensional shape to uniquely define a right side and a left part of a circumferential zone when the wearable element is worn. The sensorized garment further includes a band carried by the circumferential zone, and at least one conductor connected between the sensor and a zone of the sensorized garment.

19 Claims, 11 Drawing Sheets

(52) U.S. Cl.
CPC ...... *A41D 2200/10* (2013.01); *A61B 2503/10* (2013.01); *A61B 2562/0261* (2013.01); *A61B 2562/12* (2013.01)

(56) References Cited

FOREIGN PATENT DOCUMENTS

| WO | WO-2014165997 A1 | * | 10/2014 | ................ A61B 5/01 |
| WO | WO-2015193045 A1 | * | 12/2015 | ................ A61B 5/01 |
| WO | WO-2016009277 A1 | * | 1/2016 | ............. A41D 1/002 |
| WO | WO-2017075703 A1 | * | 5/2017 | ........... A41C 3/0057 |

\* cited by examiner

SENSORIZED GARMENT

CROSS REFERENCE TO THE RELATED APPLICATIONS

This application is the national stage entry of International Application No. PCT/IB2019/060496, filed on Dec. 5, 2019, which is based upon and claims priority to Italian Patent Application No. 102018000010886 filed on Dec. 7, 2018, the entire contents of which are incorporated herein by reference.

TECHNICAL FIELD

The present invention relates to a garment at least in part in contact with the skin and sensorized to detect biometric parameters. Non-limiting examples of the use of the garment according to the present invention are sporting activities and the work environment, for example both in the white-collar and blue-collar sectors, to monitor, among others, parameters indicative of the level of attention, of stress level, as well as directly related to the state of health of the individual in a more clinical sense etc.

BACKGROUND

It is known to apply sensors to detect biometric parameters, in particular electrodes, to a garment to detect, for example, the bioelectric signal associated with cardiac activity. A problem encountered with known systems relates to providing a reliable acquisition of signals in many conditions of the user, from sports training, to carrying out work activities such as those of white collars or blue collars.

A need is also felt to keep the pressure of the electrode or, in general, of the sensor on the skin above a predetermined level and, at the same time, to reduce or avoid discomfort for the user due to skin contact with the electrode. This is in fact a compromise between the stability of the signal generated by the electrode and the comfort of use of the garment.

A further requirement is to provide a signal conditioning and processing system generated by the sensors that improves the ease of use of the garment both in sports and in the workplace.

SUMMARY

The object of the present invention is to satisfy at least in part one or more of the aforementioned requirements.

The object of the present invention is achieved by means of a sensorized garment comprising: a wearable element in contact with the skin and having a circumferential area surrounding a body part in use;
  A band carried by the circumferential zone, the band having a first and a second portion of ends mobile with respect to each other while the wearable element is worn;
  A clamping device for tightening the band by hand on the body part by acting on the first and second end portion so that the band is circumferentially stretched on the skin in use when the clamping device is tightened and the band is loose around the portion of the body to facilitate wearing when the clamping device is released;
  At least one sensor applied on the band and arranged for use on the skin to detect parameters upon tightening of the clamping device;
  At least one conductor connected between the sensor and a zone of the garment configured to carry a control unit programmed to process/transmit the sensor signal transmitted via the conductor;
  in which the wearable element has a three-dimensional shape shaped to uniquely define a right side and a left part of the circumferential area when it is worn.

This garment allows the sensor to be tightened firmly to the skin in particular through the action of the band which performs the function of a belt adjustable by the user and of the three-dimensional conformation of the wearable element which allows a solid anchorage to the body part even in case of sudden or particularly wide movements, as can happen both during the performance of physical activities and work activities, such as the visual inspection in person in narrow places. It has been verified that the analysis of the signals generated by the sensors is greatly improved when the latter maintain a stable position on the skin during use. This is particularly important, for example, when specific sensors are used as electrodes for measuring the electrocardiographic signal. In this case, in fact, the sensors must, in addition, maintain a precise position on the trunk or torso of the individual, to generate signals with reduced artefacts and a morphology suitable for a subsequent analysis.

Moreover, the garment is suitable for many types of electrodes to detect biometric parameters. Preferably electrodes are used comprising electrically conductive polymers which are flexible and have reduced thickness so as to increase comfort when the garment is worn and the wearable element is narrow. The garment can be worn on different areas of the body depending on the applied biometric sensors and is in particular a tank top or a top having a portion configured to be worn on at least one shoulder and the circumferential area is configured to surround the trunk or torso. In this case, the sensors are in contact with the trunk. This allows the electrode to detect, for example, signals for an electrocardiographic signal analysis, to calculate heart rate or respiratory rate.

When the sensor is an electrode comprising an electrically conductive polymer, it is preferable that the band comprises at least one zone having a first percentage elongation and a zone having a second percentage elongation in which, for the same load, the first elongation is lower than the second elongation and that the electrode is applied to the area having the first elongation. Preferably, the first elongation is substantially null so as not to damage the electrode when the closure device is tightened.

In fact, it is important for integrity and a long useful life of the sensor, that the latter be applied in areas of limited extensibility or percentage elongation at least in the circumferential direction, i.e. in the direction of greater load when the closure device is tightened. Excessive deformations of the sensor application area can in fact damage the sensor and/or alter its response over time as a function of a variable contact surface and/or compromise the anchoring to the wearable element, reducing the useful life or requiring frequent maintenance.

According to a preferred embodiment, the conductive polymer comprises polyethylenedioxythiophene: sulfonated polystyrene, hereinafter PEDOT: PSS, and at least one of dimethylsulfoxide DMSO and ethylene glycol EG, preferably the former in greater quantities by weight than the latter.

This particular composition makes it possible to detect electrophysiological signals useful for visual inspection, automatic analysis or through which to calculate aggregate parameters such as heart rate or others.

According to a preferred embodiment, an estensimetric sensor or strain gauge is attached to the garment through at least a clamp, preferably manufactured by 3D printing. Clamps are easily attached, i.e. by sewing or thermosbonding to the garment and 3D printing provides a high flexibility to adapt the dimensions of the clamps to different sizes of the garment. The estensimetric sensor is preferably applied to the zone of the band having the second percentage elongation, in particular if the first elongation is zero.

According to a preferred embodiment, the garment comprises an external garment to which the wearable element is fixed and arranged on the opposite side of the skin with respect to the wearable element and having circumferential dimensions, when the garment is not worn, equal to or greater than those of the band when the closure device is tightened.

The external garment is for example a T-shirt, a shirt or other garment of known production process and distribution to which the sensorized wearable element is connected for example for use in the field of control of biometric parameters of staff during working hours in offices, warehouses, shops etc. Furthermore, the presence of the external garment makes it possible to minimize or completely cancel the visual impact from the outside of the sensor so that the latter is barely visible or completely hidden from view when the garment is worn. The garment may comprise either the wearable element alone or the combination of the external garment and the wearable element. According to a preferred embodiment, the external garment defines an opening superimposed on or facing the closure device to allow direct manual access to the latter when the garment is worn, Preferably, the opening can be closed, for example by means of a zipper, a hook and loop fastener, snap-buttons or the like.

According to a preferred embodiment, a sensor to measure the respiratory rate comprises an elongated element of an electrically conducting polymeric material.

According to a preferred embodiment, the garment is also equipped with the electronic control unit to acquire and process the signals coming from the sensors, suitably programmed to calculate both the heart rate and the respiratory rate through a single differential derivative obtained by means of at least one pair of electrodes, or the respiratory one through a signal coming from a further sensor, for example an extensometer that measures the deformation of the wearable element in relation to the respiratory act.

In particular, the algorithms implemented in the control unit are such as to require a relatively small computing power and therefore allow the realization of the control unit with inexpensive technologies, at the same time ensuring real-time performance.

BRIEF DESCRIPTION OF THE DRAWINGS

The present invention will be described hereinafter by some preferred embodiments, given by way of non-limiting examples, with reference to the attached drawings. These drawings illustrate different aspects and examples of the present invention and, where appropriate, structures, components, materials and/or similar elements in different figures are indicated by similar reference numbers.

In particular.

DETAILED DESCRIPTION OF THE EMBODIMENTS

Figure 1:
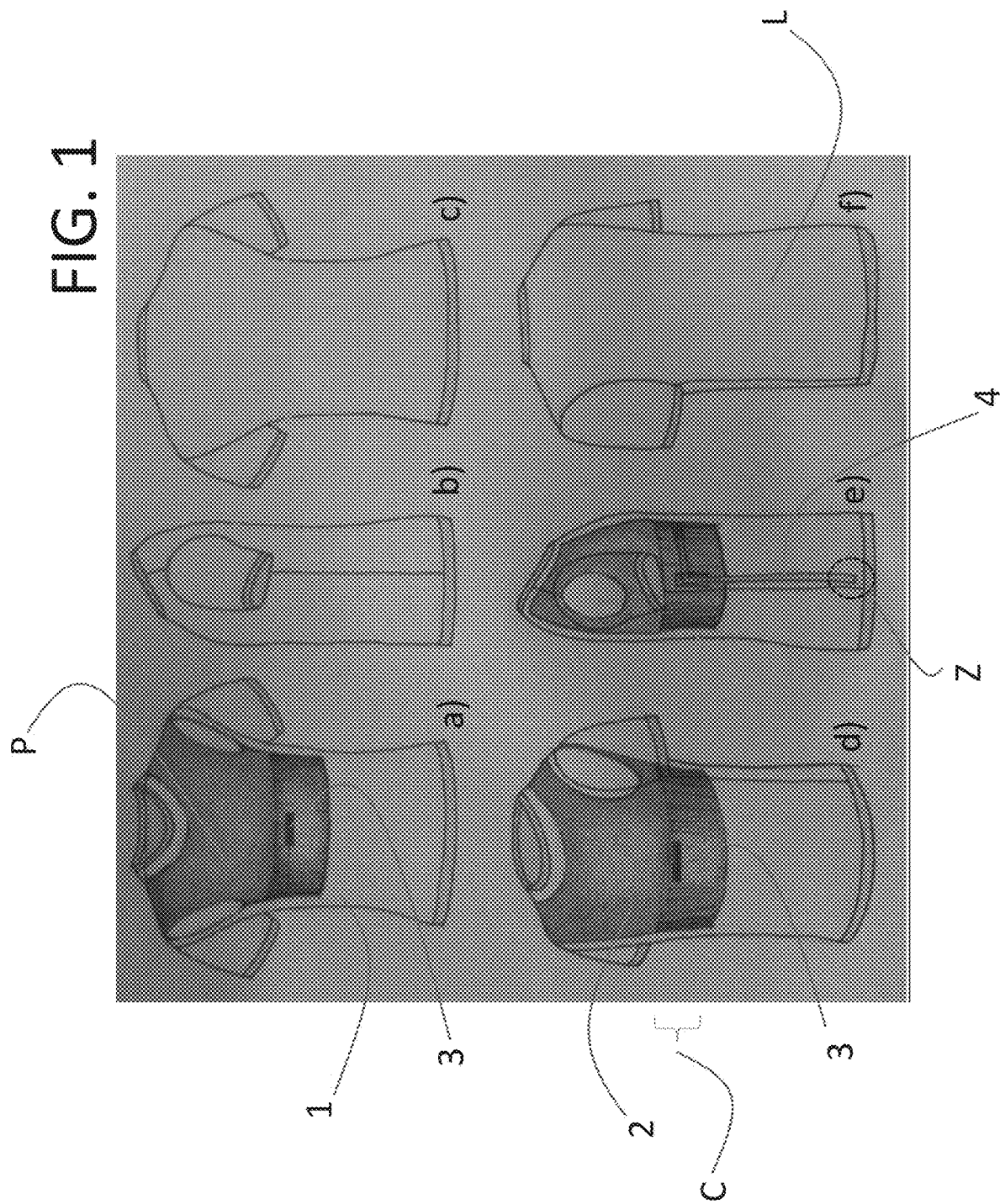
FIG. 1 shows sketches of a garment, in a clockwise direction, front view with external garment and wearable element in evidence a), side view of the external garment only b), rear view of the external garment only c), view in three-quarters of external garment and wearable element d), side view of garment and wearable element e) and rear view of three-quarters of the external garment alone f)

Number 1 in FIG. 1 indicates a sensorized garment comprising a wearable element 2 and, according to a preferred embodiment, an external garment IL. The garment L is worn on the opposite side of the skin with respect to the wearable element and can have any type of finish, for example to be a T-shirt of a covering fabric as illustrated in the figures or also by means of a material having the appearance of a net and therefore at least partially transparent.

The wearable element 2 has a three-dimensional shape suitable for unambiguously defining a right side and a left side when it is worn so as to provide an effective anchorage even in case of repeated, wide or sudden movements during use. For example, wearable element 2 is configured to be worn on the trunk or torso and define, with various geometries both symmetrical and asymmetrical, a top or a tank top.

Moreover, wearable element 2 comprises a circumferential zone C for surrounding a portion of the body, for example the trunk, having a substantially flat band and having at least one substantially undeformable area or sector at least in the circumferential direction. This can be achieved according to numerous embodiments suitable for industrialization in the field of garment manufacturing, for example by means of strips of fabric sewn together and/or with further portions IP of a fabric suitable for contact with the skin, even a simple cotton fabric, which defines the aforementioned three-dimensional shape, or by means of molded or extruded polymeric strips connected to the further portions P of the wearable element, for example by heat sealing and/or sewing. According to most of these variants, the material defining the chemical composition and/or the shape of the band, e.g. extrusion, fabric, etc. is different from the material of portions P. In particular, the latter have the main function of a garment, e.g. comfort, sweat absorption, perspiration etc. and the band has a support and anchorage function. In the example of FIG. 1, the portions P define, as a whole, an upper opening for the head and two lateral openings for inserting the arms.

Figure 4:
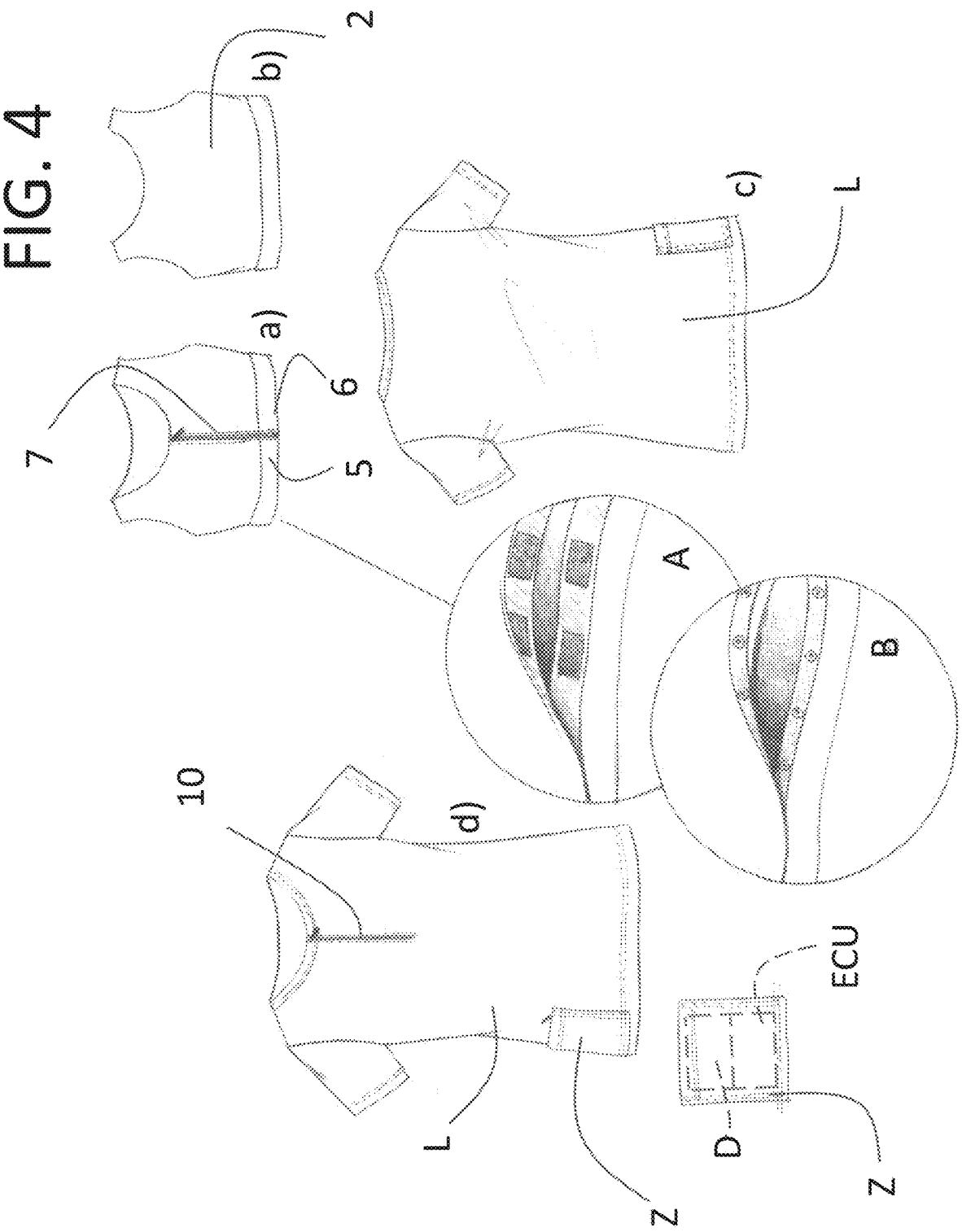
FIGS. 4 to 8 illustrate clockwise, for respective alternative embodiments, a front view of the wearable element a), a rear view of the wearable element b), a rear view of the external garment c), a front view of the external garment d), a detail of the wearable element according to a first embodiment A and a second embodiment B, and a detail of the external garment.
Figure 5:
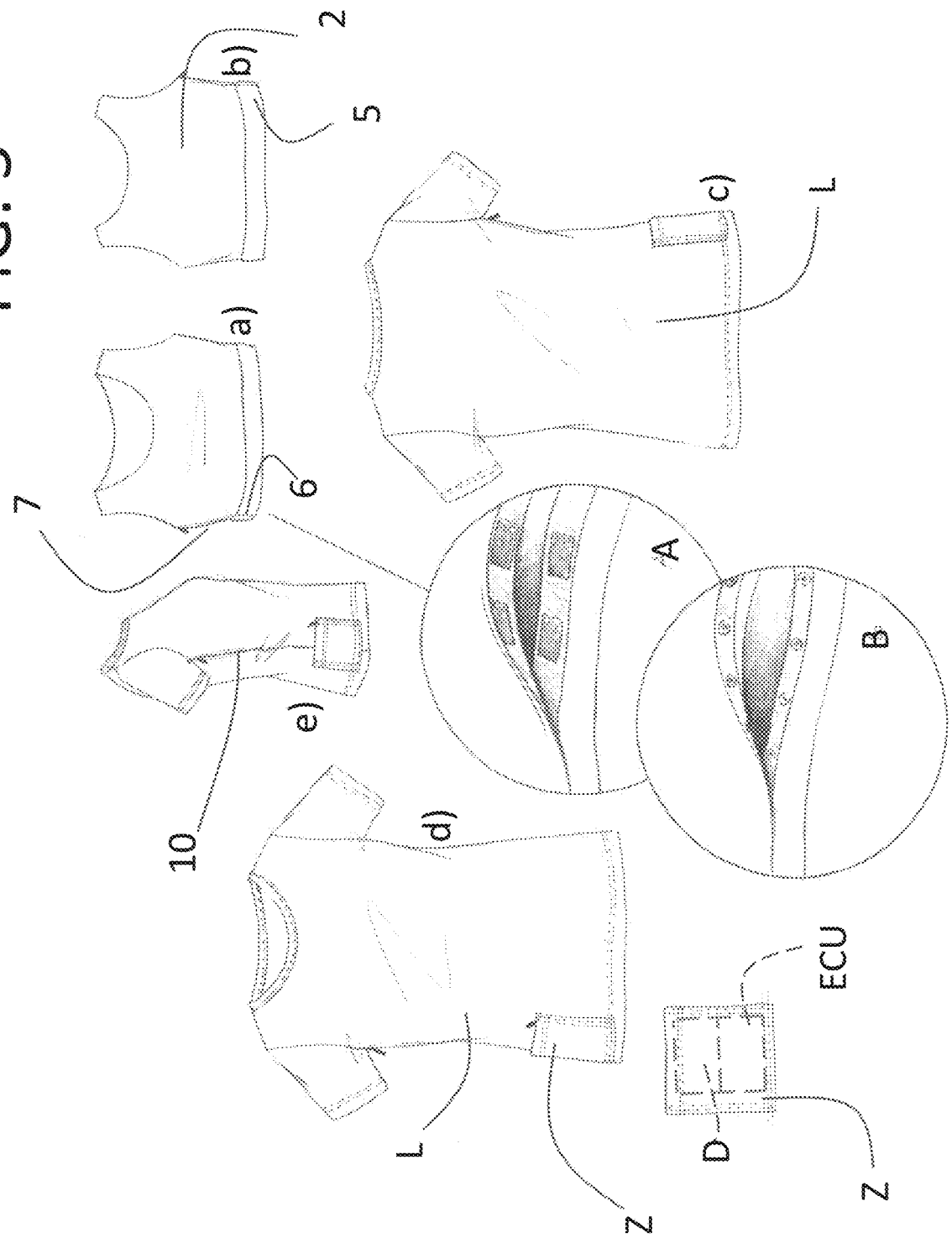
Figure 6:
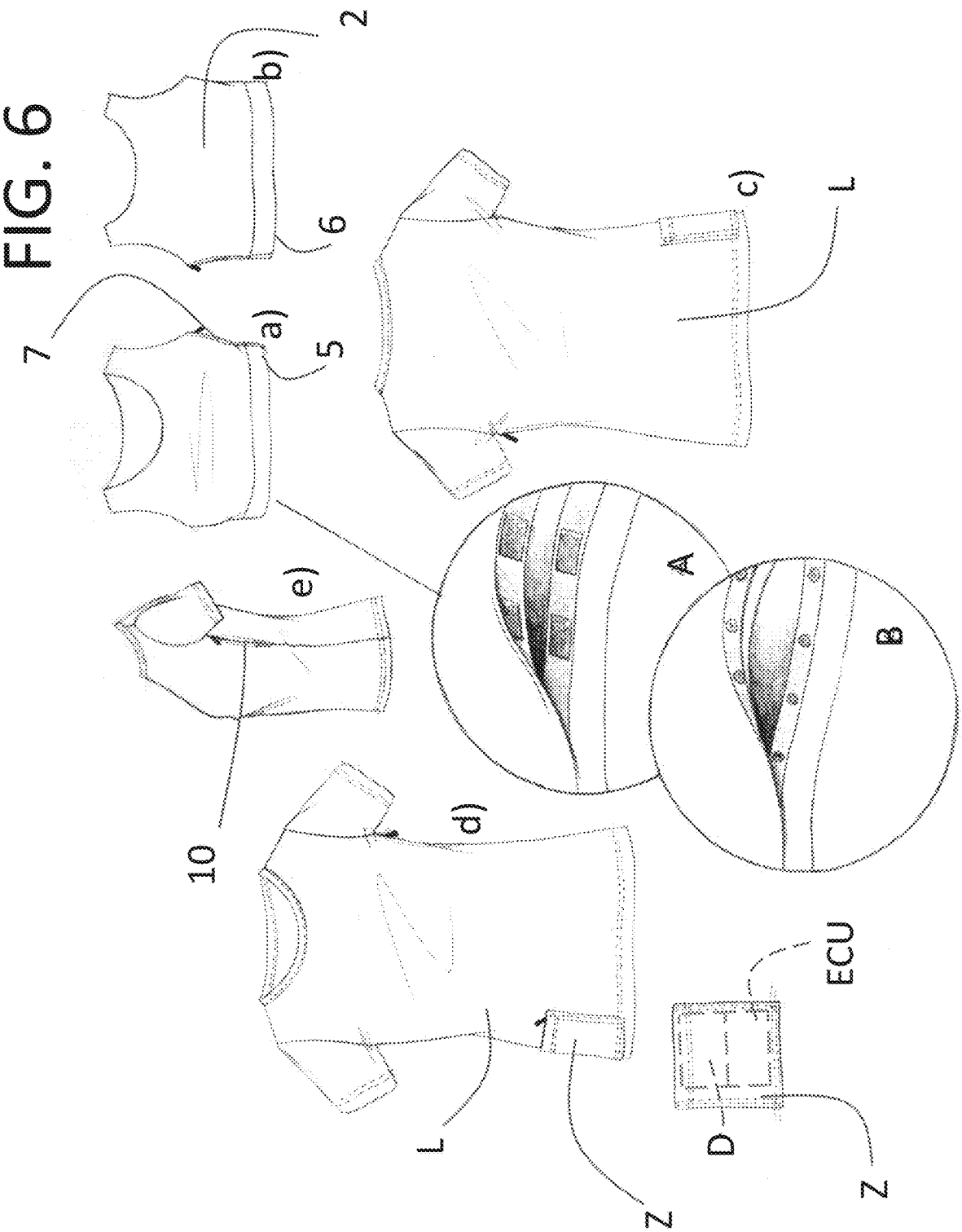
Figure 7:
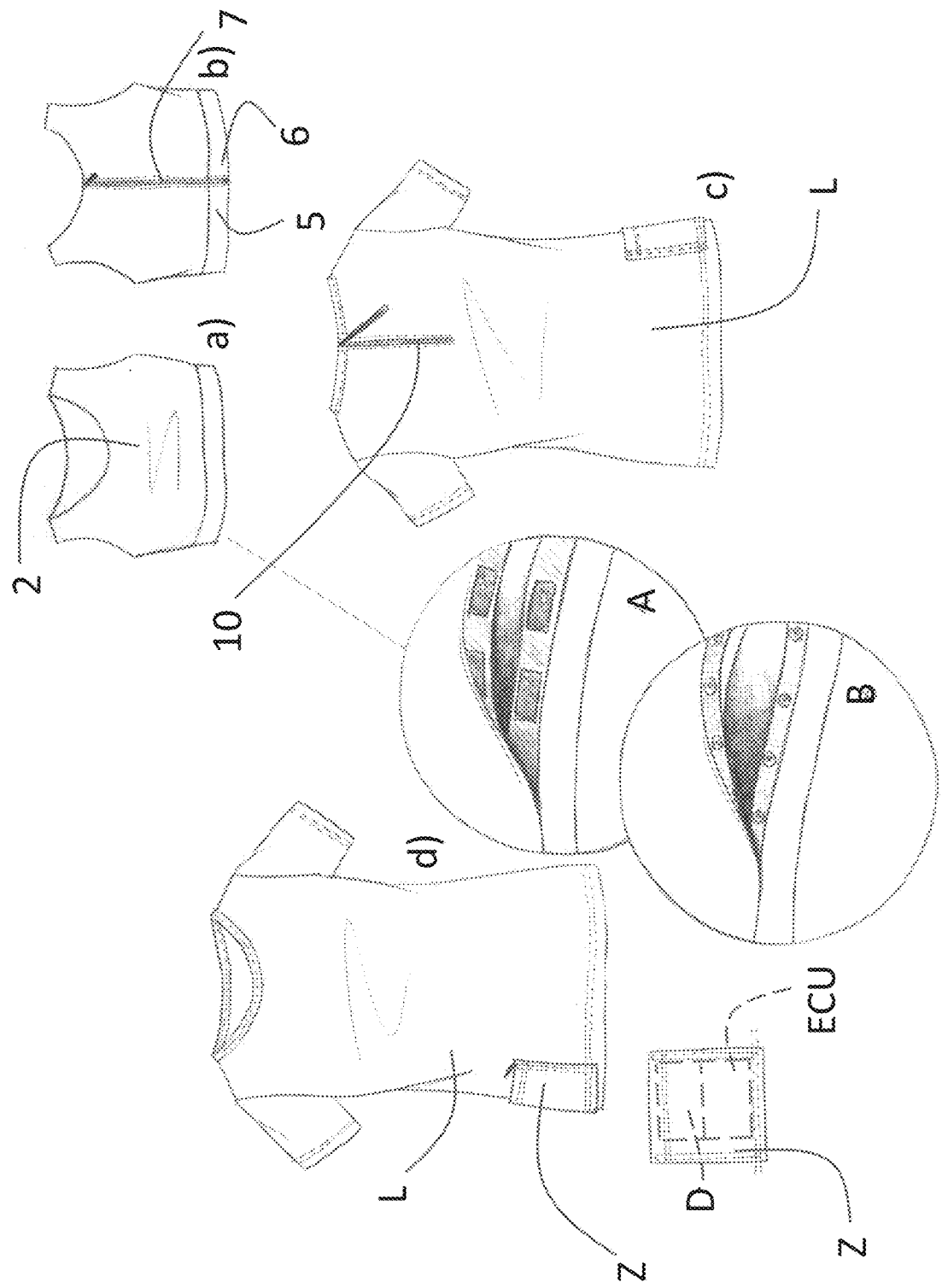
Figure 8:
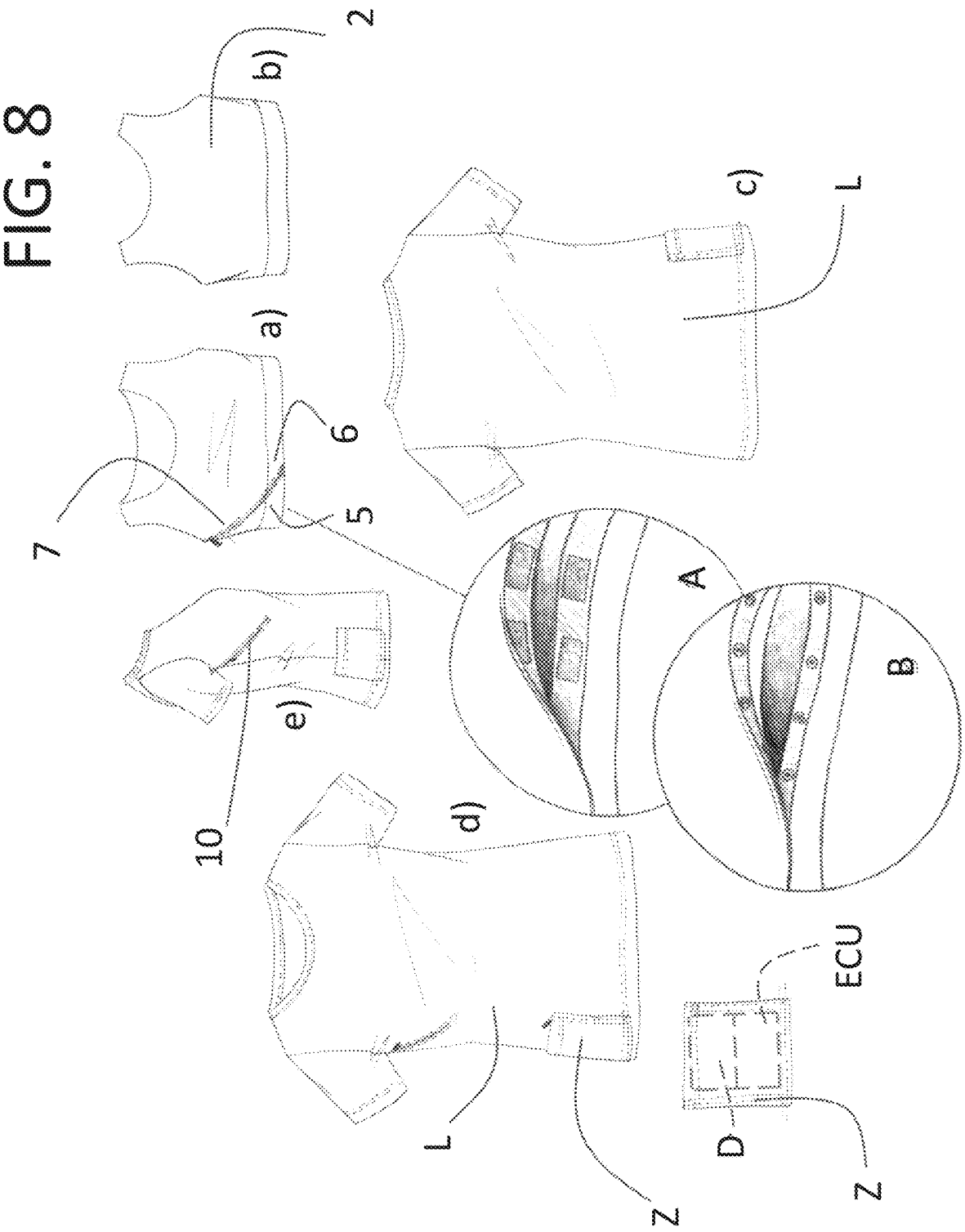

As shown in FIG. 4, the band comprises a first and a second end portion 5, 6 cooperating with a closure device 7 to adjust, and in particular to tighten in a circumferential direction, the band and increase the adherence of the latter to the skin.

Closure device 7 can be made in various ways, both 'open/closed' and continuously adjustable, for example by means of a zipper in which each side is fixed to the relative end portion 5, 6, snap-buttons or traditional button/buttonholes applied on the end portions, a slot carried by an end portion and cooperating with the other end portion in a sliding manner so as to be subsequently fixed by a hooks and loopholes strip, through laces between the end portions 5, 6 and fixed either by means of a knot or through a slider element with or without a spring commonly used to adjust in the circumferential direction windbreakers and/or the tension of sports shoe laces etc. In general, the band is such that the first and second end portions 5, 6 face each other in a circumferential direction and approach each other when the closure device 7 is tightened.

In particular, the closure device 7 is manually adjustable between a loose configuration in which the band is not stretched and the wearable element is easily worn, and a tightened configuration in which the band is stretched in a circumferential direction to apply a desired and sufficient pressure on the skin.

As shown in FIG. 1, on at least a substantially inextensible zone of the band, or in any case in an area having a percentage elongation in the circumferential direction, for the same load, lower than that of other zones of the band, a sensor 3 is applied comprising preferably an electrically conductive polymer that, by means of the pressure applied to the skin by closure device 7, keeps the sensor in position for detecting an electrophysiological signal and/or an impedance from which a cardiac and/or respiratory rate can be subsequently calculated, as will be described below. According to a preferred embodiment (FIG. 2) there are at least three electrodes for measuring a signal representative of the heart rate, preferably arranged two on the front and one on the back of the band.

It should be noted that the term sensor must be understood in a generic way also comprising more than one electrode or sensing element.

As illustrated in the figures, external garment L has a length, in the direction in which the garment is worn, greater than that of wearable element 2 so that, during the wearing operation, the user grasps an external garment that is distal from wearable element 2 and, therefore, avoids unwanted touching of the band and in particular of sensor 3.

Through the possibility of wearing the garment by gripping external garment L, the circumferential area of wearable element 2 is not normally grasped, thus preserving the sensors from premature wear due to contact with the hands and/or fingers and/or nails of the user.

According to the embodiments illustrated especially in FIGS. 4 to 8, closure device 7 is arranged either on a right or left side or in a central area rear or front of the circumferential zone with reference to the condition worn so as to have an easy manual closure.

Moreover, external garment L in turn defines an opening 10 superimposed on or facing closure device 7 to allow access and hand-adjustment of the latter. Preferably, the opening 10 is closed by a zip, hook and loophole strips, snap-buttons etc. and is opened to allow closure device 7 to be tightened or released.

Figure 2:
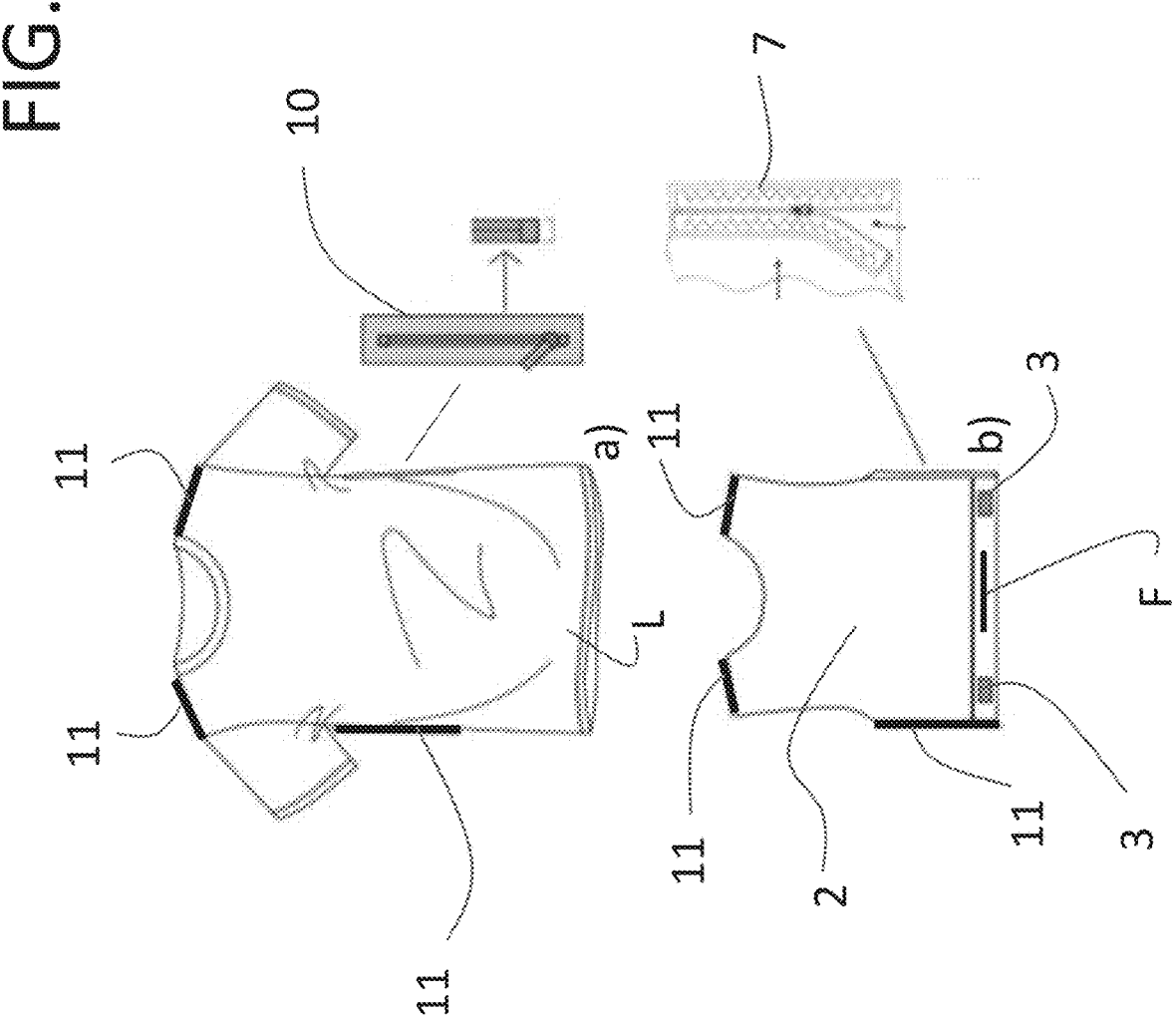
FIG. 2 illustrates sketches of the external garment a) separated from the wearable element b) with some enlarged details and in a front perspective.

FIG. 2 shows a possible arrangement of connection lines 11 between wearable element 2 and external garment L. These lines or zones define a mechanical connection between the wearable element and garment L to allow the garment to be jointly worn and took-off when the user grabs external garment L to wear or take-off the garment, An example of mechanical connection is a seam or other another connection used in clothes.

According to a preferred embodiment of the present invention, the electrically conductive polymer comprises polyethylenedioxythiophene and sulfonated polystyrene.

According to a preferred embodiment of the present invention, the weight ratio between polyethylenedioxythiophene and sulfonated polystyrene is between 1 and 20, even more preferably 2.5. In this way the deposition on the woven substrate as a thin film is particularly simple and with an adequate impedance for the acquisition of a cardiac electrophysiological signal or for the measurement of the respiratory frequency or rate.

According to a preferred embodiment of the present invention, the electrode is manufactured so as to further include dimethylsulfoxide and/or ethylene glycol and/or sorbitol. Alternatively or in combination, it is also possible to functionalize the polymer using metal nanoparticles such as Ag, Au, Ag/AgCl. It is also possible to add the polymer by means of a crosslinker, for example (3-glycidyloxypropyl trimestoxysilane (GLYMO) to improve the mechanical characteristics, and/or a surfactant such as Triton X or p-dodecylbenzenesulfonic (DBSA), to improve the application on the band via e.g. screen printing.

Figure 3:
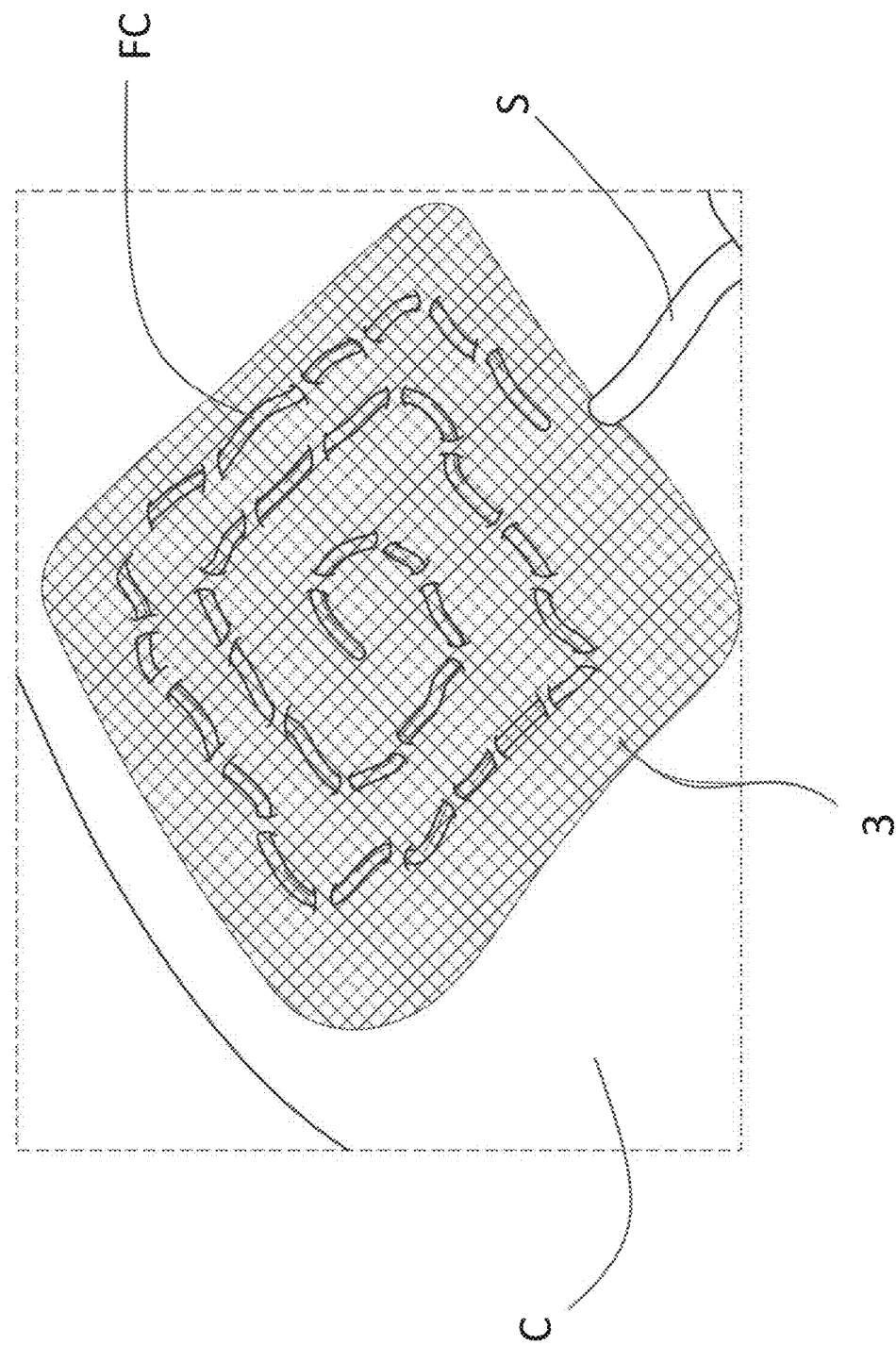
FIG. 3 shows an enlarged detail of a preferred embodiment of electrical connection between a sensor and a textile conductor.

The electrically conductive polymer constituting impedance sensor 3 is preferably applied by screen printing (FIG. 3) to the substantially inextensible areas but other techniques of application on the band are possible.

Sensor 3 is electrically connected by elongated or filament-like conductors FC to a zone Z configured to carry an electronic acquisition unit D programmed to process/transmit the signal and calculate at least the heart rate and/or respiratory rate.

Such conductors can be made according to various alternatives which include, in an exemplary and non-exhaustive embodiment, a weft or warp thread of external garment L and/or of the electrically conductive wearable element 2 since it comprises at least one metal strand, for example of copper, silver or stainless steel, e.g. 316L stainless steel, or because coated with a metal layer, for example silver, or an electrically conductive polymer. For example, the resistivity is 12 or lower, preferably 10 ohms per foot.

According to a preferred embodiment of the present invention, the filament-like conductor FC is sheathed along at least a portion, preferably for most of the length between the sensor 3 and the zone Z. The sheath S is of an electrically insulating material and, according to a not limiting example, this is a heat-shrinking material for example activated at temperatures of about 70-80°. When sheathed, conductor FC is attached to wearable element 2 and external garment L via a sewn hole or is housed in a sewn fabric channel. An example of such a channel is shown in details A and B of FIGS. 4-8.

This minimizes interference that disturbs electrical signal processing.

Furthermore, filament-like conductor FC is textile (see FIG. 3), i.e. it can be sewn, so that it can be fixed to/on sensor 3, in order to transmit the electrical signal by direct contact with the electrode. For example, conductor FC is a cotton thread with additives of aluminum nanoparticles having a plurality of twisted strands so as to allow use in a normal industrial sewing machine. Also other filament-like conductors are sewable, in particular the thread including metal strands e.g. a stainless steel strand.

It is also possible to use copper or silver nanoparticles in addition to or replacing aluminum ones. Preferably, zone Z is carried by external garment L and the electrical continuity of the filament-like conductors FC is maintained through connection lines 11 between wearable element 2 and zone Z. For example, as shown in FIG. 1, conductor FC, preferably sheathed, is supported by wearable element 2 and, through sewn connection line 11 is then supported by external garment L for connection to zone Z. Connection of filament-like conductors FC to acquisition device D is preferably obtained via a plug, e.g. a USB plug having a number of pins compatible with sensor or sensors 3. For example, when heart rate is measured by three electrodes and respiratory frequency is measured via a variable impendence sensor (as explained below in greater detail), the plug has at least 5 pins.

In general, the respiratory rate can be measured in various ways, through the evaluation of the effects that this produces on physical quantities that can be measured more or less invasively. Examples are the use of oronasal thermocouples, flow meters, thoracic/abdominal bands with resistive or inductive strain gauges, variations in thorax impedance, etc. The last two examples are those best applicable to the case of a garment for measuring physiological parameters. In the case of a strain gauge sensor, inhalation produces an elongation of the sensor, mounted on an extensible part of a chest band, with consequent variation of the reference electrical parameter (resistance, impedance, capacity). An electrical extensometer is characterized by two fundamental quantities: the resistance of the wire of the sensitive element and the 'gauge factor' or transduction factor, which expresses the sensitivity of the extensometer.

The increase in resistance of the strain gauge is expressed as a ratio between the change in resistance and the total resistance of the wire.

Figure 9:
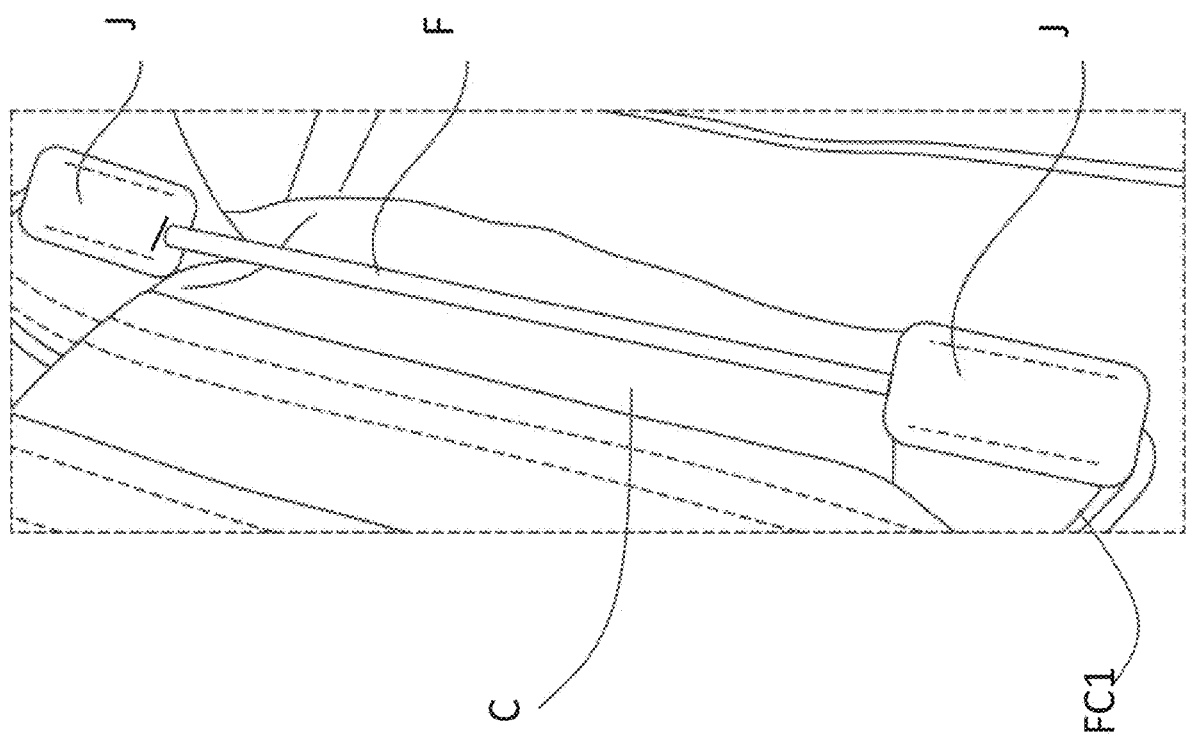
FIG. 9 shows an enlarged detail of an embodiment of a strain gauge sensor for detecting the respiratory rate.

FIG. 9 shows a preferred embodiment in which the strain gauge sensor F is filiform or band-like made of an electrically conductive polymer, for example an electrically conductive polymer of commercial availability. The wire or band is fixed to the garment by means of a junction element J, preferably of an electrically insulating material. According to the example shown in the figure, at each end of the strain gauge sensor, each junction element—in particular designed and manufactured by 3D printing to allow greater production flexibility for geometrical differences due to the various sizes of the garment—embeds an end portion of strain-gauge sensor F and an end portion of a filament-like conductor FC1, preferably made of the same material of conductor FC. Therefore strain gauge sensor F and filament-like conductor FC1 are electrically connected inside junction element J e.g. via direct contact. Furthermore, junction element J is connected, e.g. sewn, to wearable element 2 in order to allow deformation, i.e. elongation, of sensor F during breathing. Preferably, between two adjacent junction elements J along the circumferential direct there is provided the area having the second percentage elongation, which is higher than the percentage elongation of the area where sensor 3 is attached.

The strain gauge sensor F is electrically connected to zone Z through filament-like conductor FC1, which is suitably sheathed for example in the same manner as conductor FC. Furthermore, filament-like conductor FC1 extends to external garment L from wearable element 2 through sewn connection line 11 as conductor FC does.

In the case of impedance measurement, it is possible to measure the signal also through the same electrodes used for measuring the electrocardiogram or other electrophysiological type signals, exploiting a stimulation signal that is out-of-band with respect to such other signals.

Impedance measurement can be performed in various ways. The main one is to inject a small alternating signal into the body through two electrodes and measure the variation of some parameters induced by the change of thoracic impedance deriving from the presence of a greater or lesser quantity of air in the thoracic cage. In an exemplary embodiment, it is possible to inject an alternating sinusoidal current signal of known amplitude and to measure the difference in electrical potential between the two electrodes. By injecting a signal at a frequency higher than that of the band of the electrophysiological signal detected with passive electrodes, it is possible, through a high pass hardware filter, to remove the electrophysiological component in the impedance measurement and at the same time (with complementary low pass filtering) to prevent that this signal injected from the outside disturbs the measure of the biopotential. The current being known and after measurement of the voltage (or vice versa), it is immediate to calculate the impedance. In another exemplary embodiment, the injected high frequency alternating signal is modulated in amplitude by the thoracic impedance change so that it is possible to demodulate this signal, filter the signal in a relatively low narrow band (typically between 2 and 4 Hz) and then process it as done with the other acquisition methods.

Therefore, according to a preferred embodiment, an electronic control unit ECU is programmed to process the signal of sensor 3 in order to calculate the respiratory frequency. The electronic control unit may be either integrated with electronic acquisition unit D and, advantageously, provided with a data storage module to store both data for the hearth rate/electrocardiogram and/or time history data about respiratory frequency. In this way, data can be download e.g. at the end of the working day. Alternatively, the electronic control unit may be embedded in another electronic device, e.g. a smartphone, a smartwatch, a tablet, a PC or the like and electronic acquisition unit D may be connected in data exchange, preferably in wireless data exchange, to the electronic device.

Preferably, the electronic control unit ECU is programmed so that a first step is the application of a high-pass filter, which in an exemplary implementation could have a cut-off frequency of 1 Hz, more generally capped so as not to cut-off the low-frequency contributions that are representative of the pseudoperiodicity of the respiratory signal. This value, which is significantly high for an algorithm for filtering respiratory signals, is particularly suitable for impedance frequency respiration measurements, by means of electrodes comprising conductive polymers, which generate signals with slow drifts and polarizations. If breath detection solutions are used using different wearable technologies (such as thoracic strain gauge sensors), this filtering could be bypassed or maintained without significantly altering the performance of the calculation.

Subsequently, a low-pass filtering step is provided, which in an exemplary implementation could be a moving average, which realizes a limitation of the signal band below 2 Hz and more generally such as to include at least the fundamental component of the respiratory pseudoperiodic signal. This value, relatively higher than the typical implementations of such algorithms, is motivated by the previous choice of high pass filtering connected to the need to exclude the typical disturbances of the impedance measurement of the breath by means of electrodes comprising conductive polymers. The importance of this filter is twofold: on the one hand it allows the elimination of the high-frequency components that certainly do not characterize the respiratory signal, including some residual electrocardiographic components that could be present when the respiratory signal is acquired by means of electrodes conductive polymer with the impedance method. Moreover, this filter limits the signal band, allowing a subsampling, which in an exemplary implementation could be around 40 Hz, more generally between 30 and 50 Hz, moreover between 10 and 100 Hz, and allows a reduction of the quantity of calculations of the control unit.

The under-sampled signal is then processed by a crest detector to identify the crests of low-frequency waves that represent inspiration. To this end, the crest detector adopts an adaptive amplitude threshold with an autoregressive approach that takes into account the last two detected crests. This adaptability is essential to ensure a detection capability even in the presence of signals with movement disorders linked to the adoption of a garment with non-adhesive electrodes in contact with the skin. The threshold can be calculated for example as 50% of the amplitude of the last crest (Cr) detected plus 25% of the last threshold value (Th):

$$Th[n]=0.5\ Cr[n-1]+0.25\ Th[n-1]$$

If no respiratory action is detected for more than a predetermined time interval (which in an exemplary implementation could be equal to 30 seconds), the algorithm lowers the threshold to a value equal to a fraction of the last value of the adopted threshold, which in an exemplary implementation could be equal to $1/64$. According to this adaptation, $Th[n-1]=Th[n]$, where $Th[n]$ represents the last value calculated as just illustrated.

A mechanism for correcting the results has also been implemented if too many crests are identified on the signal in physiologically inadmissible time intervals. This defines an upper limit to the detectable respiration rate, which can be adapted to the specific needs. For example, in an exemplary solution, this limit can be estimated so as to guarantee a maximum detectable frequency of about 2 breaths per second.

Finally, the final respiratory rate is evaluated starting from the average of the last respiratory acts, which could be four in an exemplary implementation, so as to limit the variability linked to local errors. This data is updated at each breath, and converted to indicate the number of breaths per minute rather than the second, in order to simplify the reading by the user.

According to a preferred embodiment, the control unit is also programmed to process the bioelectric signal in order to calculate a heart rate based on a variant of the pan and Tompkins algorithm for detecting the QRS complex of the electrocardiographic signal. When the control unit ECU is also programmed to calculate the respiration rate, the following additions are specifically provided. An adaptive amplitude threshold is used which takes into account the peak R just found and the previous peak R (which in an exemplary implementation could respectively be 50% of the peak just found plus 25% of the peak previously found). If no peak is found for more than a certain time interval, for example 3 seconds, the threshold is reset (to a percentage of the penultimate peak detected, for example 25%), so that the disturbances caused by the use of the conductive polymer electrodes placed on the band do not damage the QRS relief.

A process has been implemented to correct the results if peaks R too close to each other are identified, so as not to consider the last peak R detected: this defines an upper limit to the detectable heart rate, which can be adapted to the needs. For example, in an exemplary solution, this limit can be estimated so as to guarantee a maximum detectable frequency of about 190 bpm.

As briefly mentioned above, the band can comprise areas of controlled elasticity on which strain gauge sensors are applied to detect the respiratory rate. When the strain gauge sensors are not present, the band can be entirely made of a substantially inextensible material in a circumferential direction.

According to a further embodiment, the calculation of the respiratory and/or cardiac frequency on the basis of the signals of the sensor 3 is performed by applications executable on a smartwatch, smartphone and other intelligent personal mobile device connected in wireless data exchange with the garment 1. In this way, the electronic control unit electrically connected to the elongated conductors and carried by the zone Z carries out the function of transmitting the wireless sensor signal 3.

Figure 10:
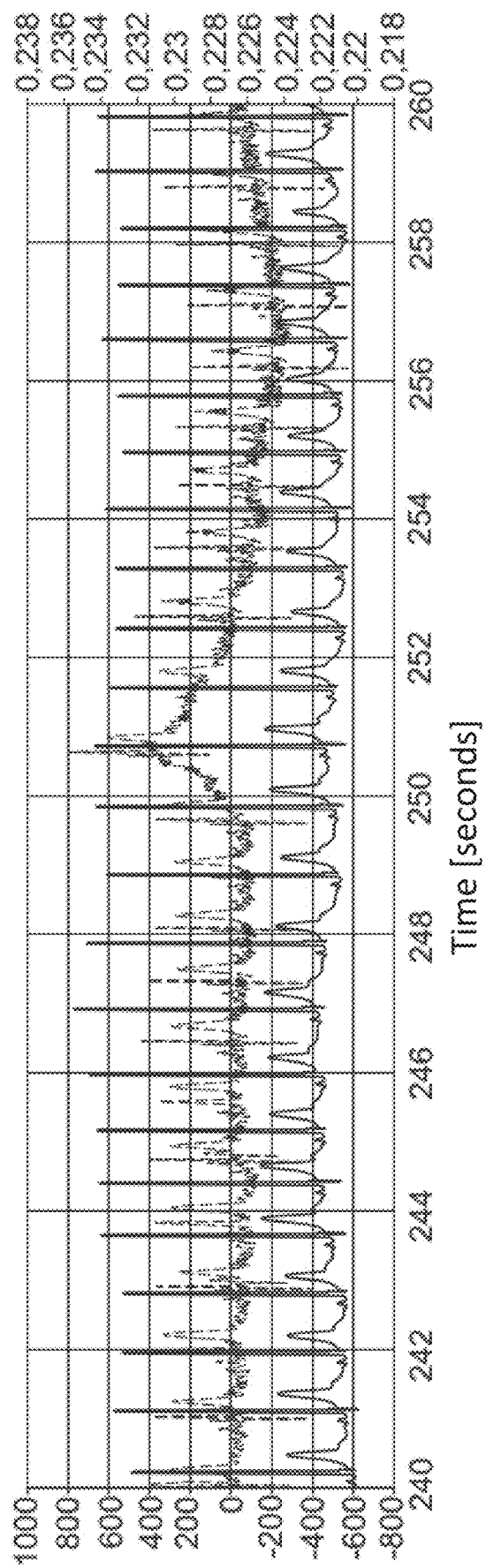
FIG. 10 is a comparative graph of an electrocardiogram detected according to an embodiment of the present invention (graph more spaced from the axis of the abscissas and in a solid line) and from a traditional electrocardiograph (graph substantially lying on the axis of the abscissas and in a dashed line)

FIG. 10 is a comparative graph between the results obtained from a sensorized t-shirt with PEDOT:PSS and DMSO electrodes, with conductors FC comprising a stainless steel strand and associated with an electronic control unit programmed to implement a Pan and Tompkins algorithm and what was obtained through a 12-lead stress electrocardiograph (Quark T12X Cosmed®) with disposable adhesive electrodes applied to the skin with gel. The heart rate calculated on the basis of the electrodes of the shirt is in substantial agreement with the relief of the electrocardiograph.

Figure 11:
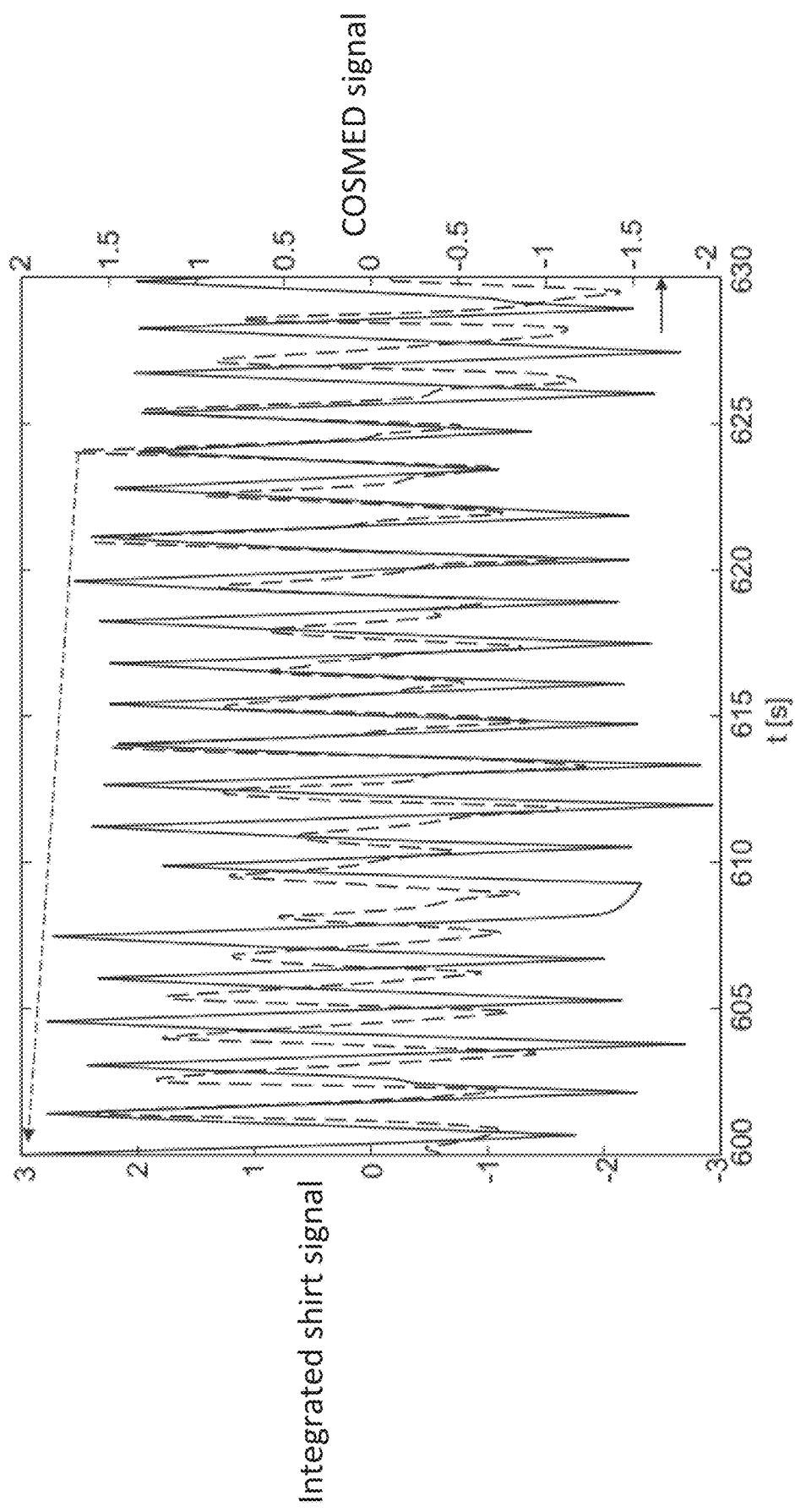
FIG. 11 is a comparative graph of respiratory acts detected according to an embodiment of the present invention (graph having a lower average oscillation amplitude and in a dashed line) and a standard pulmonary activity measuring device (graph having a greater average oscillation amplitude and in a solid line).

FIG. 11 is a comparative graph between what is obtained from a sensorized t-shirt using strain gauge F applied on band 3, with conductors with stainless steel strand and what was obtained by means of a volume meter of air exchanged during breathing comprising a mask in which the user breathes and a measuring instrument connected to the mask through tubes, for example a meter made by Cosmed®. The agreement is good and there is an average error of −5.2% between the figure of the shirt and that of the air volume meter.

What is claimed is:
1. A sensorized garment, comprising:
  a wearable element, wherein in use, the wearable element is configured to contact a skin and has a circumferential zone surrounding a part of a body;
  a band, wherein the band is carried by the circumferential zone, the band comprises a first end portion and a second end portion moving relative to each other while the wearable element is worn;
  a closure device for hand-tightening the band on a body part and acting on the first end portion and the second end portion, wherein the band is in a circumferential tension contacting the skin in use when the closure device is tightened and the band is loose around a portion of the body to facilitate wearing when the closure device is released;
  at least one sensor applied on the band to detect upon tightening of the closure device;
  at least one conductor, wherein the at least one conductor is connected between the at least one sensor and a zone of the sensorized garment, and is configured with an electronic control unit programmed to process a sensor signal carrying a QRS complex electrocardiographic signal transmitted through the at least one conductor by performing analysis of the QRS complex electrocardiographic signal to identify a heart rate having beat-to-beat variability by applying an adaptive threshold on at least two most recent R peaks in the QRS complex electrocardiographic signal, the adaptive threshold calculated by taking a first percentage of a most recent R peak to provide a first term and a second percentage of a second most recent R peak to provide a second term, where the second percentage is less than the first percentage, adding the first and second terms together thereby calculating the adaptive threshold;

wherein the wearable element has a three-dimensional (3D) shape to uniquely define a right side and a left part of the circumferential zone when the wearable element is worn;

wherein the wearable element is configured to be worn on a trunk and the band is tightened by the closure device, wherein the at least one sensor generates the QRS complex electrocardiographic signal and a respiration signal; and wherein the electronic control unit is connected in data exchange to the at least one sensor and the electronic control unit is programmed to perform a signal analysis on the respiration signal within a predetermined frequency range to obtain a respiratory rate value using a respiratory adaptive amplitude threshold.

2. The sensorized garment according to claim 1, wherein the at least one sensor comprises a pair of electrodes contacting the skin and an electrically conductive polymer for measuring either a biopotential or an impedance, wherein the band comprises a first zone having a first percentage elongation and a second zone having a second percentage elongation, for a same load on the first zone and the second zone, the first percentage elongation is lower than the second percentage elongation, and wherein an electrode of the pair of electrodes is applied on the first zone.

3. The sensorized garment according to claim 2, wherein the electrically conductive polymer comprises polyethylenedioxythiophene sulfonated polystyrene and, furthermore, one of dimethylsulfoxide, ethylene glycol, or sorbitol.

4. The sensorized garment according to claim 1, wherein the band comprises at least one elastic zone in a circumferential direction and at least one strain gauge sensor applied to the at least one elastic zone.

5. The sensorized garment according to claim 4, wherein the at least one strain gauge sensor is electrically connected to a further filament-like conductor within at least one junction element manufactured by a 3D printing.

6. The sensorized garment according to claim 4, wherein the at least one strain gauge sensor comprises an elongated element made of an electrically conductive polymer.

7. The sensorized garment according to claim 6, wherein the wearable element is configured to be worn on a trunk of an individual and the band is tightened by the closure device, wherein the at least one strain gauge sensor generates a signal representative of a respiratory rate on a basis of a circumferential deformation of the at least one elastic zone when the individual breathes.

8. The sensorized garment according to claim 1, wherein the at least one conductor is sewable and comprises either fibers of a natural or synthetic non-electrically conductive material added to metal nanoparticles, or a metallic strand, wherein the metal nanoparticles are at least one of aluminum, copper and silver.

9. The sensorized garment according to claim 1, comprising an external garment attached to the wearable element to be disposed in use on an opposite side of the skin with respect to the wearable element and comprising an opening substantially superimposed on the closure device when the sensorized garment is worn to make the closure device accessible and hand-tightenable or releasable.

10. The sensorized garment according to claim 9, wherein the external garment is attached to the wearable element to be fluctuating with respect to the band when the closure device is tightened.

11. The sensorized garment according to claim 1, wherein the signal analysis performed on the respiration signal to obtain the respiratory rate value is by applying a high-pass filter at a frequency no higher than at 2 Hz and a low-pass filter at a frequency between 10 and 100 Hz using the respiratory adaptive amplitude threshold.

12. The sensorized garment according to claim 11, wherein the electronic control unit is further programmed to calculate the adaptive threshold with at least one additional term corresponding to at least one additional percentage of at least one additional R peak that is prior to the second most recent R peak in the QRS complex electrocardiographic signal, wherein each additional percentage is less than the second percentage, wherein the adaptive threshold is further calculated by adding each additional term to the first term and second term.

13. The sensorized garment according claim 2, wherein the band comprises at least one elastic zone in a circumferential direction and at least one strain gauge sensor applied to the at least one elastic zone.

14. The sensorized garment according claim 3, wherein the band comprises at least one elastic zone in a circumferential direction and at least one strain gauge sensor applied to the at least one elastic zone.

15. The sensorized garment according to claim 5, wherein the at least one strain gauge sensor comprises an elongated element made of an electrically conductive polymer.

16. The sensorized garment according to claim 3, wherein the wearable element is configured to be worn on a trunk and the band is tightened by the closure device, wherein the at least one sensor generates a signal representative of an electrocardiogram and respiration.

17. The sensorized garment according to claim 4, wherein the wearable element is configured to be worn on a trunk and the band is tightened by the closure device, wherein the at least one sensor generates a signal representative of an electrocardiogram and respiration.

18. The sensorized garment according to claim 5, wherein the wearable element is configured to be worn on a trunk and the band is tightened by the closure device, wherein the at least one sensor generates a signal representative of an electrocardiogram and respiration.

19. The sensorized garment according to claim 6, wherein the wearable element is configured to be worn on a trunk and the band is tightened by the closure device, wherein the at least one sensor generates a signal representative of an electrocardiogram and respiration.

* * * * *